United States Patent [19]
Brennan et al.

[11] 4,095,022
[45] June 13, 1978

[54] PRODUCTION OF BIS-(MORPHOLINO-N-ALKYL) ETHERS

[75] Inventors: Michael E. Brennan; Philip H. Moss; Ernest L. Yeakey, all of Austin, Tex.

[73] Assignee: Texaco Development Corporation, New York, N.Y.

[21] Appl. No.: 679,590

[22] Filed: Apr. 23, 1976

Related U.S. Application Data

[62] Division of Ser. No. 583,014, Jun. 2, 1975, Pat. No. 4,026,935.

[51] Int. Cl.$^2$ .......................................... C07D 265/28
[52] U.S. Cl. .................................................. 544/87
[58] Field of Search ......... 260/268 SY, 246 B, 584 C; 544/87

[56] References Cited

U.S. PATENT DOCUMENTS

| | | | |
|---|---|---|---|
| 3,112,317 | 11/1963 | Marschall et al. | 260/268 SY |
| 4,026,935 | 5/1977 | Brennan et al. | 544/87 |

*Primary Examiner*—Jose Tovar
*Attorney, Agent, or Firm*—Carl G. Ries; Thomas H. Whaley

[57] ABSTRACT

An improved process is disclosed for selectively producing a bis-(morpholino-N-alkyl) ether directly from the corresponding N-(hydroxyalkyl)morpholine compound. The improved process includes contacting the N-(hydroxyalkyl)morpholine compound with a catalytically effective amount of a silica-alumina or certain phosphorus containing substances at a temperature of about 200° C to 300° C under a pressure sufficient to maintain the mixture substantially in liquid phase and recovering from the resultant reaction mixture the bis-(morpholino-N-alkyl) ether.

According to the preferred embodiment, N-(2-hydroxyethyl)morpholine is heated in the presence of a catalytic amount of a silica-alumina catalyst having an alumina content of from about 5 to about 50 wt. % at temperatures of from about 240° C to about 290° C in liquid phase to selectively produce the corresponding N,N',2,2'-dimorpholinodiethyl ether (DMDEE).

13 Claims, No Drawings

PRODUCTION OF BIS-(MORPHOLINO-N-ALKYL) ETHERS

This is a division of application Ser. No. 583,014, filed June 2, 1975, now U.S. Pat. No. 4,026,935, granted May 31, 1977.

BACKGROUND OF THE INVENTION

1. Field of the Invention

The instant invention generally relates to an improved process for producing bis-(morpholino-N-alkyl) ethers directly from the corresponding N-(hydroxyalkyl)-morpholine compound; and more particularly, to an improved liquid phase process for selectively producing bis-(morpholino-N-alkyl) ethers in the presence of certain specific catalytically effective substances.

2. Prior Art

Bis-(morpholino-N-alkyl) ethers are generally well-known compounds having established utility as polyurethane catalysts. Generally the entire class of these compounds is useful in catalyzing urethane systems including the C-alkyl substituted bis-(morpholino-N-alkyl) ether compounds wherein one or both of the morpholine moieties contain C-(substituted) alkyl radicals on one or more of the carbon atoms and/or wherein the N-alkyl moiety is either a branched or straight chain radical containing from 1 to about 10 carbon atoms.

Bis-(morpholino-N-alkyl) ethers have been prepared by many methods. Examples of some of the more well-known methods are disclosed in U.S. Pat. No. 3,787,354. In on method for DMDEE synthesis, N-(2-chloroethyl)morpholine is reacted with N-(2-hydroxyethyl)morpholine (HEM) and sodium. See, for example, J. Amer. Chem. Soc., 62, 1448 (1940) and Aeta Chem. Scand., 8, 350 (1954). Another method involves the reaction of triethanolamine in the presence of hydrochloric acid. See, for example, J. Pharm. Soc. Japan, 75, 1367 (1955). Still another method involves the reaction of morpholine with bis-(2-chloroethyl)ether. See, for example, Bull. Soc. Chim. France, 3537 (1965). Many of these processes involve caustic neutralization with attendant problems or require the use of excess reagents to react with liberated chlorine compounds. In addition, these methods involve the use of difficulty obtainable chemical intermediates such as raw materials and/or produce the desired product in low yield wherein the reaction product mixture contains by-products which are difficult to separate by known methods.

Another method involves the vapor phase reaction of N-(2-hydroxyethyl)morpholine (HEM) in the presence of an activated alumina catalyst to form DMDEE. See, for example, J. Amer. Chem. Soc., 63, 298 (1941). This method suffers the attendant problems of vapor phase synthesis with low yields and extensive by-product formation.

Unexpectedly it has been found that bis-(morpholino-N-alkyl) ethers can be selectively produced directly from the readily available corresponding N-(hydroxyalkyl)morpholine in liquid phase without the attendant deficiencies of previously known processes. Under rigorous reaction conditions, i.e. temperatures in the 200° C to 300° C range, the inventive process is surprisingly selective to the desired product. The expected extensive decomposition and concomitant production of unwanted side products is minimized. Additionally, the compounds effective in catalyzing the synthesis of the instant invention are readily available. Another outstanding advantage resides in the fact that the most prevalent by-product of the instant process is the corresponding N,N'-dimorpholino-$\alpha,\omega$-alkane. While the production of this by-product is insubstantial, i.e. from 1:10 to 1:20 or higher with respect to the desired product, it need not be removed from the final product. These N,N'-dimorpholino-$\alpha,\omega$-alkane compounds are non-deleterious to urethane systems and in fact act as a co-catalyst with the bis-(morpholino-N-alkyl) ethers for polyol-isocyanate reactions.

SUMMARY OF THE INVENTION

In accordance with the broad aspect of the invention, bis-(morpholino-N-alkyl) ether compounds are selectively produced directly from the corresponding N-(hydroxyalkyl) morpholine in a catalyzed reaction process which includes initially contacting the corresponding N-(hydroxyalkyl)morpholine with a catalytically effective amount of silica-alumina or certain phosphorus containing substances at temperatures of from about 200° C to 300° C while reaction pressures sufficient to retain the mixture substantially in liquid phase are maintained and then recovering the bis-(morpholino-N-alkyl) ether from the resultant reaction mixture.

In accordance with the invention, the bis-(morpholino-N-alkyl) ether compound produced is a result of the bimolecular dehydration of two N-(hydroxyalkyl)morpholine molecules. Thus, by varying the N-(hydroxyalkyl)morpholine reactant utilized, one may achieve, for example the C-alkyl substituted bis-(morpholino-N-alkyl) ether. Additionally, by varying the chain length or the branched configuration of the N-alkyl moiety, one may achieve bis-(morpholino-N-alkyl) ethers having the corresponding di-N-alkyl moieties.

DESCRIPTION OF THE PREFERRED EMBODIMENTS

In accordance with a preferred embodiment, an N-(hydroxyalkyl)morpholine compound is continuously fed into a fixed bed reactor at space velocities of from 0.2 to about 2.0 g/ml catalyst/hr at temperatures of from about 240° C to 280° C. A fixed bed of silica-alumina is employed containing from 10 to about 40 wt. % alumina and having a surface area of from about 50 m²/g to about 700 m²/g. The reactor pressure is maintained at about 100 psig. The liquid effluent is collected and purified according to standard distillation techniques.

In accordance with one preferred method, the starting reactant and residual water are removed by vacuum stripping and the remainder of the reaction product is used as a polyurethane catalyst without need for further refining of the product.

The N-(hydroxyalkyl)morpholine compounds that can be utilized are depicted by the formula:

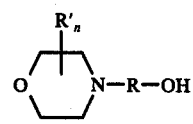

wherein R is a straight chain or a branched alkyl radical of from about 2 to about 10 carbon atoms, R' is a lower alkyl radical such as methyl, ethyl and the like and n is an integer from 0 to 4. Illustrative of the N-(hydroxyalkyl)morpholines are N-(2-hydroxyethyl)morpholine, N-(3-hydroxypropyl)morpholine, N-(2-hydroxypropyl)morpholine, N-(2-hydroxyethyl)-2-methylmorpholine, N-(2-hydroxyethyl)-2,6-dimethylmorpholine, and the like. Preferred N-(hydroxyalkyl)morpholines are of the above formula wherein R is an alkyl radical of from about 2 to about 4 carbon atoms. Especially preferred are N-(hydroxy-alkyl)morpholines of the above formula wherein R is an alkyl radical of from about 2 to about 3 carbon atoms, and n is 0. Most preferred is N-(2-hydroxyethyl)morpholine.

The catalysts which are useful in practicing the process of this invention include silica-aluminas, and certain phosphorus-containing substances. The silica-aluminas which are effective as catalysts include those having an alumina content of from about 5 to about 50 wt. % alumina and preferably from about 10 to about 40 wt. % alumina. While silica or alumina utilized alone have proven to be poor catalysts for the process of this invention, the silica-aluminas as herein described affect the bimolecular dehydration of N-(hydroxyalkyl)morpholines in high yields and with high selectivity to the desired product.

While most any silica-alumina with an alumina content within the above-mentioned range is effective as a catalyst in the process of this invention, particularly desirable are silica-aluminas with surface areas of from about 50 m$^2$/g to about 700 m$^2$/g.

The silica-alumina catalysts can be employed in any well known form such as a fine powder or as a pellet. Pelletized catalysts are particularly suitable for continuous processes in which the catalyst may be employed as a fixed bed. The particular physical form in which the catalyst is employed is not critical in the process of this invention.

Suitable phosphorus-containing substances which can be employed include, for example, acidic metal phosphates, phosphoric acid compounds and their anhydrides, phosphorous acid compounds and anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

More particularly, suitable acidic metal phosphates include boron phosphate, ferric phosphate, aluminum phosphate, and the like.

Suitable phosphoric acid compounds include aqueous or anhydrous phosphoric acids such as orthophosphoric acid, pyrophosphoric acid, metaphosphoric acid, hypophosphoric acid, and condensed phosphoric acids such as polyphosphoric acids. Accordingly, an example of a suitable phosphorous acid is orthophosphorous acid. Additionally, phosphoric acid-impregnated silicas having from about 10 to about 30 wt. % phosphoric acid may be employed.

In addition, any commercially available mono-, di-, or tri-alkyl or aryl phosphate or phosphite ester can be employed as the catalyst in the inventive process. Additionally, bis(phosphates) and secondary phosphate esters such as those disclosed in U.S. 3,869,526 and U.S. 3,869,527, respectively, can be used. Preferably, the lower alkyl esters are employed such as those having from 1 to about 8 carbon atoms per alkyl group. Preferred aryl esters contain from about 6 to about 20 carbon atoms and may include a phenyl group or alkyl-substituted phenyl group.

Further, suitable alkyl of aryl substituted phosphorous and phosphoric acids which may be employed as a catalyst include alkyl phosphonic acids, aryl phosphonic acids, alkyl phosphinic acids and aryl phosphinic acids. Preferably, such acids include alkyl groups having from 1 to about 8 carbon atoms and/or aryl groups having from about 6 to about 20 carbon atoms in each alkyl or aryl group, respectively.

Specific examples of alkyl and aryl substituted phosphorous and phosphoric acids that may be used in accordance with the invention are phenylphosphinic acid, ethylphosphonic acid, phenylphosphonic acid, naphthaphosphonic acid, and methylphosphinic acid. Examples of the alkyl and aryl substituted phosphorous and phosphoric acid esters are methylphenyl phosphonate, dimethylphenyl phosphonate, methylphenyl phosphinate, ethyl naphthaphosphinate, and propylmethyl phosphonate. When phosphorous acid is employed, it is preferably used in an anhydrous form or in an aqueous solution having from about 10 to about 70 wt. % phosphorous acid. The aqueous phosphorous acid catalyst is miscible with the reactants and is, therefore, a homogeneous catalyst.

The above-mentioned phosphorus containing substances are not intended to be exhaustive of those that can be employed as a catalyst in the instant inventive process. Those materials set forth are merely intended to be representative of the types of substances that have been found to be particularly effective. Of the substances and the types of compounds mentioned, it is particularly preferred to employ those that are known to be most reactive, such as orthophosphoric acids, polyphosphoric acids, boron phosphate, aluminum phosphate, ferric phosphate, and orthophosphorous acid. Of these, the most preferred is orthophosphorous acid.

The amount of catalyst employed in the process of this invention will depend, of course, on the type of catalyst and the particular reactants involved. In batch processes, silica-alumina catalysts in an amount of from about 1 to about 20 wt. %, based upon the amount of reactants present, has been found satisfactory, with an amount of from about 5 to about 10 wt. % being preferred. In a continuous reaction process wherein the catalyst is generally employed as a fixed bed, a weight hourly space velocity (WHSV) of from about 0.1 to about 5.0 g/ml catalyst/hr. is satisfactory with a space velocity of from about 0.2 to about 2.0 g/ml catalyst/hr. being preferred.

The phosphoric acid-impregnated silicas, ferric phosphate, boron phosphate, and aluminum phosphate are effective catalysts when employed in substantially the same amounts as the silica-alumina catalysts. The aqueous phosphorous acid catalyst is slightly more active than the other catalysts and is generally employed in an amount of from about 1 to about 10 wt. %, based on the reactants present, with an amount of from about 2.5 to about 5.0 wt. %, on the same basis, being preferred.

The bimolecular dehydration reaction of this invention, as described herein, is carried out substantially in a liquid phase reaction which is conducted at a temperature of from about 200° C to about 300° C. The exact temperature range selected is somewhat empirical and will depend upon the particular reactants employed and the desired conversion levels. It has been found that temperatures in the range of from about 240° C to 280° C are normally sufficient for good yield production of the desired bis-(morpholino-N-alkyl) ether. When N,N',2,2'-dimorpholinodiethyl ether (DMDEE) is produced, temperatures in the range of 255° C to 265° C are most preferred.

The pressure at which the reaction is carried out can be at any pressure sufficient to maintain the reactants substantially in the liquid state. Generally, reaction pressures of from about 10 to about 1,000 psig. have been found satisfactory. However, there is no incentive to employ reaction pressures higher than is necessary to maintain the reactants and products substantially in the liquid state. By substantially in the liquid state is meant the following. As has been discussed previously, water is formed as a co-product of the bimolecular condensation reaction. It has been found advantageous in batch processes to maintain the water content of the reaction system at as low a level as is possible in order to enhance catalytic activity and simultaneously to shift the reaction equilibrium toward the desired product. Therefore, it is desirable to maintain the reaction zone at a pressure such that the water formed in the bimolecular condensation reaction will be removed from the reaction zone as a vapor. It has been found that for typical reaction temperatures in the range of from about 200° C to about 300° C the preferable reaction zone pressure is from about 10 to about 100 psig, with pressures of about 50 psig being most preferred.

In practicing the process of this invention a solvent is not required, but may be employed if desired. Whenever a solvent is employed, the solvent should be nondeleterious to the reaction environment and the desired reaction. Examples of suitable solvents include hydrocarbon solvents such as hexane, decane, dodecene, benzene, and the like, and chlorinated aromatic solvents such as chlorobenzene. Whenever a solvent is employed in the process of this invention, the amount employed should be maintained at a minimum whenever bis-(morpholino-N-alkyl) ether is the desired product, because the presence of substantial amounts of solvent tend to favor the formation of the dimorpholinoalkane.

The crude reaction product obtained from the process of this invention will contain the desired bis-(morpholino-N-alkyl) ether in combination with some dimorpholinoalkane, a small amount of heavy materials and unreacted N-(hydroxyalkyl) morpholine. In batch processes where a heterogeneous catalyst is employed in intimate admixture with the reactants, the catalyst will be present in the crude reaction mixture. It has been found that the catalyst may be recovered from the crude reaction mixture and recycled for reuse according to the process of this invention. In the case of heterogeneous catalysts, excepting the phosphoric acid-impregnated silicas, it is generally preferable to wash the recovered catalyst, for example with methanol and/or water, and dry it prior to recycling it for reuse. In the case of the aqueous phosphorous acid catalyst, it may be recovered and reconstituted to the desired concentration prior to reuse as an amine salt and reused as such.

The bis-(morpholino-N-alkyl) ether can be recovered from the crude reaction mixture by conventional means, for example distillation, extraction, and the like. Similarly, the unreacted N-(hydroxyalkyl)morpholine compound may be recovered and recycled for conversion to the desired product according to the process of this invention.

In accordance with another aspect of the instant invention, the small amount of dimorpholinoalkane produced as a by-product of the instant process need not be removed. Specifically, it is known that dimorpholinoalkane compounds also act as catalysts in urethane systems. These compounds contain greater amine equivalents per gram than do their bis-(morpholino-N-alkyl) ether counterparts owing to reduced molecular weight of the molecular while amine content remains identical to that of the ether.

Thus, in accordance with this aspect, the amine equivalent per gram of the urethane catalyst produced can be effectively varied, by varying the reaction conditions of the instant process to produce relatively more or less of the dimorpholinoalkane compounds. Thus, the problems associated with mixing and blending suitable bis-(morpholino-N-alkyl) ether/dimorpholinoalkane catalysts are essentially alleviated.

When the process of the instant invention is practiced in order to achieve a catalytic mixture or to produce predominantly the bis-(morpholino-N-alkyl) ether, the crude reaction product need only be vacuum stripped under conditions from about 760 mm Hg/255° C to 1.0 mm Hg/60° C to effect removal of the ureacted reagent and the residual water of reaction. Thus, the need for expensive fractional distillation or the like is alleviated.

The process of this invention will now be further illustrated in the following examples which are for the purpose of illustration and should not be considered a limitation on the scope of the invention.

EXAMPLES 1-7

A series of experiments was performed wherein N-(2-hydroxyethyl)morpholine was charged to a 1-liter stirred autoclave along with an amount of material being evaluated as a catalyst. The autoclave was then padded with nitrogen, heated to the indicated temperature and maintained at this temperature for the indicated period. Thereafter, the contents of the autoclave were recovered and subjected to gas-liquid chromatographic analysis to determine the amount of N-(2-hydroxyethyl)morpholine (HEM) converted as well as the amount of N,N',2,2'-dimorpholinodiethylether (DMDEE) and 1,2-dimorpholinoethane (DMORE) produced. The data are presented in the following Table 1. From an examination of this data it is apparent that the silica-alumina catalyst (Aerocat ® TA) was quite active and selective for the formation of DMDEE, whereas the acid clay catalyst (Superfiltrol) was not selective and the cationic ion-exchange resin (Amberlyst 15) was inactive.

TABLE 1

| Example No. | HEM, moles | Catalyst Type | Wt. % | Temp., °C | Pressure psig | Time, hrs. | % HEM conversion | Selectivity % DMDEE | DMORE | DMDEE DMORE |
|---|---|---|---|---|---|---|---|---|---|---|
| 1 | 1.81 | Aerocat®TA[1] | 10.0 | 260 | 90-202 | 6.0 | 65.7 | 83.5 | 14.3 | 5.8 |
| 2 | 2.47 | Aerocat TA | 10.0 | 220 | 27-60 | 6.0 | 16.8 | 94.2 | 5.8 | 16.3 |
| 3 | 1.94 | Aerocat TA | 10.0 | 300 | 290-890 | 6.0 | 100.0 | 16.4 | Mostly lights | |
| 4 | 1.47 | Aerocat TA | 20.0 | 260 | 138-240 | 4.0 | 71.4 | 31.9 | 16.5 | 5.0 |
| 5 | 2.58 | Superfiltrol[2] | 10.0 | 220 | 36-56 | 6.0 | 4.0 | 34.9 | 62.3 | 0.56 |
| 6 | 1.84 | Superfiltrol | 10.0 | 300 | 100-1000 | 6.0 | 100.0 | 8.2 | Mostly lights | |

TABLE 1-continued

| Example No. | HEM, moles | Catalyst Type | Wt. % | Temp., °C | Pressure psig | Time, hrs. | % HEM conversion | Selectivity % DMDEE | DMORE | DMDEE DMORE |
|---|---|---|---|---|---|---|---|---|---|---|
| 7 | 1.04 | Amberlyst 15[3] | 13.5 | 105–178 | — | 1.6 | 0.0 | No reaction | | |

[1] Silica-alumina catalyst, 74.4% silica, 25.0% alumina, 0.6% other oxides, surface area 550–700 m$^2$/g sold by American Cyanamid Co., Bound Brook, N. J. 08805
[2] Superfiltrol acid clay, grade 1 sold by Filtrol Corporation, 250 East Washington Boulevard, Los Angeles, Calif. 90023
[3] Cationic ion-exchange resin sold by Rohm & Haas Co., Independence Mall West, Philadelphia, Pa. 19105

EXAMPLES 8–14

According to the general procedure of Examples 1–7, a number of other materials were evaluated for effectiveness in catalyzing the reaction of HEM to DMDEE. These data are presented in the following Table 2. From an examination of the data, it is apparent that all of the silica-aluminas (Examples 8 and 14) were of high activity and selectivity in catalyzing the formation of DMDEE, whereas alumina, silica, acid clay, activated charcoal, and silicon carbide were relatively inactive and/or non-selective for the formation of DMDEE.

TABLE 2

| Ex. No. | HEM, moles | Catalyst Type | wt.% | Temp., °C.[1] | Time, hrs. | % HEM conv. | Lts. (H$_2$O, etc.) | Effluent, Glc A%[2] HEM | By-products[10] | DMORE | DMDEE | Hvya. | DMDEE DMORE |
|---|---|---|---|---|---|---|---|---|---|---|---|---|---|
| 8 | 3.50 | 980-25[3] | 5.0 | 260 | 5.0 | 80.3 | 4.8 | 19.7 | 0.2 | 3.3 | 75.8 | 1.0 | 23.0 |
| 9 | 3.50 | T-126[4] | 5.0 | 260 | 5.0 | 14.4 | 0.5 | 85.6 | 1.0 | 3.5 | 9.1 | 0.3 | 2.6 |
| 10 | 3.50 | KA[5] | 5.0 | 260 | 5.0 | 2.5 | 0.2 | 97.5 | 0.0 | ~0.8 | 1.5 | t | 1.9 |
| 11 | 3.50 | AC[6] | 5.0 | 260 | 5.0 | 4.7 | 0.5 | 95.3 | 0.1 | 1.6 | 0.7 | 0.5 | 0.4 |
| 12 | 3.50 | T-869, -1571[7] | 5.0 | 260 | 4.0 | 2.4 | 0.2 | 97.6 | 0.1 | 1.0 | 1.1 | 0.1 | 1.0 |
| 13 | 3.50 | AL-0104T[8] | 5.0 | 261 | 5.0 | 3.2 | 0.5 | 96.8 | 0.2 | 0.8 | 1.3 | 0.4 | 1.6 |
| 14 | 3.50 | 979[9] | 5.0 | 260 | 5.0 | 78.3 | 0.1 | 21.7 | 0.1 | 3.0 | 74.4 | 0.7 | 24.8 |

Footnotes for Table 2
[1] Back-pressure regulator set at ca. 50 psig.
[2] Vented material disregarded; ranged from 0.0 to 4.8% of liquid charge and consisted of approximately 20 to 85% water.
[3] Davison silica-alumina, 25% Al$_2$O$_3$; 325 m$^2$/g surface area sold by W. R. Grace & Co., Davison Chemical Division, 101 North Charles Street, Baltimore, Md. 21203.
[4] Gamma-alumina; 216 m$^2$/g surface area sold by Girdler Chemical, Inc., Louisville, Ky. 40201.
[5] Girdler montmorillonite acid clays sold by Girdler Chemial, Inc., Lousiville, Ky. 40201.
[6] Activated charcoal sold by Pittsburgh Activated Carbon, Division Calgon Corp., P. O. Box 1346, Pittsburgh, Pa. 15230.
[7] Girdler silicas; results are average for two separate runs surface areas, 63 and 131 m$^2$/g respectively.
[8] 99% alumina; 80–100 m$^2$/g surface area sold by The Harshaw Chemical Co., Division of Kewanee Oil Co., 1945 East 97th St., Cleveland, Ohio 44106.
[9] Silica-alumina, 13% Al$_2$O$_3$, 400 m$^2$/g surface area sold by W. R. Grace & Co., Davison Chemical Division, 101 North Charles Street, Baltimore, Md. 21203.
[10] Morpholine derivatives predominantly aminoethoxyethylmorpholine and hydroxyethoxyethylmorpholine.

EXAMPLES 15–24

In these examples three different silica-alumina catalysts were evaluated in a continuous process wherein the catalyst was employed in a 500 ml tubular reactor and HEM was passed over the catalyst at the temperatures, pressures and space velocities indicated in the following Tables 3 and 4. In each run the reactor effluent was analyzed by gas-liquid chromatographic techniques to determine the conversion level of HEM and the selectivity to DMDEE and DMORE. The higher space velocities produced a higher DMDEE/DMORE ratio. Additionally, the HSA-300 silica-alumina catalyst material used in Examples 21–24 was subjected to approximately 10 days of run time with no appreciable deterioration of activity.

TABLE 3

| Example No. | Catalyst | Avg. temp., °C. | Avg. press., psig | SV g/ml cat./hr. | % HEM conv. | Effluent, Glc A% HEM | DMORE | DMDEE | Hvys. | DMDEE DMORE |
|---|---|---|---|---|---|---|---|---|---|---|
| 15 | Girdler T-1219[1] | 260 | 100 | 1.02 | 18.2 | 81.8 | 1.7 | 16.2 | 0.1 | 9.50 |
| 16 | " | 260 | 100 | 0.25 | 43.1 | 56.9 | 4.5 | 34.0 | 0.9 | 7.60 |
| 17 | ACCO Ext. 25[2] | 260 | 111 | 0.98 | 31.7 | 68.3 | 1.4 | 29.2 | <0.1 | 20.8 |
| 18 | " | 264 | 108 | 0.24 | 68.9 | 31.1 | 5.2 | 56.6 | 1.7 | 10.9 |
| 19 | " | 268 | 115 | 1.47 | 27.9 | 72.1 | 1.3 | 25.6 | — | 19.7 |
| 20 | " | 270 | 114 | 0.47 | 54.5 | 45.5 | 3.1 | 47.0 | 0.8 | 15.2 |

[1] Girdler silica-alumina, 102 m$^2$/g surface area sold by Girdler Chemical, Inc., Lousiville, Ky 40201
[2] A pelleted form of Aerocat® TA, 25.0% Al$_2$O$_3$ sold by American Cyanamid Co., Bound Brook, N. J. 08805

TABLE 4

| Example No. | Catalyst | Avg. temp., °C. | Avg. press., psig | SV g/ml cat/hr. | % HEM conv. | Effluent, Glc A% HEM | DMORE | DMDEE | Hvys. | DMDEE DMORE |
|---|---|---|---|---|---|---|---|---|---|---|
| 21 | HSA-300[3] | 262 | 100 | 1.01 | 36.0 | 64.0 | 1.5 | 32.5 | 0.4 | 21.70 |
| 22 | " | 262 | 100 | 0.24 | 64.3 | 35.7 | 4.8 | 52.9 | 2.1 | 11.00 |
| 23 | " | 269 | 100 | 1.02 | 38.0 | 62.0 | 2.0 | 34.1 | 0.4 | 17.00 |
| 24 | " | 272 | 100 | 0.25 | 68.6 | 31.4 | 9.2 | 51.3 | 2.7 | 5.60 |

[3] Houdry HSA-300 Silica-alumina, 12.4% Al$_2$O$_3$; 290–315 m$^2$/g surface area sold by Air Products and Chemicals, Inc., Houdry Division, 1339 Chestnut St., Philadelphia, Pa. 19107

EXAMPLES 25–28

In these examples the general procedure of Examples 1–7 was followed, except that various changes in operating variables were investigated. In all runs the catalyst employed was Aerocat® TA/silica-alumina. The data are presented in the following Table 5. Examples 25–27 illustrate that within this broad range of catalyst concentrations the most preferred concentration appears to be at approximately 5 wt. % based on the total weight of reactants. At catalyst concentrations below this level there is a decrease in the HEM conversion level. At concentrations of 10% or higher there is only a slight improvement in the conversion level and a decrease in the ratio of DMDEE to DMORE. Example 28 illustrates that at 5 wt. % silica-alumina in the reaction mixture a residence time in the reaction zone of as little as 2.5 hours is sufficient to give a high conversion of HEM to the desired products.

is to bis-(morpholino-N-alkyl) ether production. These examples were run in accordance with the general procedure of Examples 1-7 using N-methyl-N-phenylethanolamine and N,N-diphenylethanolamine as the respective starting materials. The results are shown in Table 7.

TABLE 7

| Example No. | Starting Material | % Conversion of Starting Material | Desired Product |
|---|---|---|---|
| 37 | N-methyl-N-phenylethanolamine | 20.0 | No discernible amount[1] |
| 38 | N,N-diphenylethanolamine | 85.0 | Trace amounts[2] |

[1]N,N'-dimethyl-N,N'-diphenylethylenediamine formed
[2]Complex reaction mixture included N-phenyl-N'-phenylethylenediamine, N,N,N',N'-tetraphenylethylenediamine, diphenylamine, and 2,2'-diphenylaminodiethylether. Evidence of extensive decomposition was noted.

TABLE 5

| Example No. | HEM, moles | Aerocat TA, wt.% | Pressure[1] psig | Time, hrs. | % HEM conversion | Effluent, Glc A% | | | | | |
|---|---|---|---|---|---|---|---|---|---|---|---|
| | | | | | | Lts. H$_2$O, etc.) | HEM | By-products[5] | DMORE | DMDEE | Hvys. |
| 25 | 1.85 | 10.0 | 50[2] | 5.0 | 85.8 | 2.0[3] | 14.2 | 0.5 | 8.4 | 72.3 | 2.6 |
| 26 | 1.85 | 5.0 | 50 | 5.0 | 82.9 | 0.9 | 17.1 | 0.3 | 5.1 | 75.2 | 1.4 |
| 27 | 1.85 | 1.0 | 50 | 7.0 | 31.0 | 1.1 | 69.0 | 0.2 | 2.5 | 26.9 | 0.3 |
| 28 | 1.85 | 5.0[4] | 50 | 2.5 | 77.6 | 0.1 | 22.4 | 0.3 | 3.4 | 72.9 | 0.8 |

Footnotes For Table 5
[1]Temperature in all runs approximately 260° C.
[2]Pressure was maintained at 50 psig by use of a back pressure regulator and vented condensate (2-4% of liquid charge; 70-90% water; 0.5% HEM lost by venting.
[3]For all runs at 50 psig, the GLC data does not include vented material.
[4]Catalyst dried at 80° C/0.3 mm for 8.0 hours.
[5]Morpholine derivatives predominantly aminoethoxyethylmorpholine and hydroxyethoxyethylmorpholine.

EXAMPLES 29-35

In these examples the general procedure of Examples 1-7 was followed except that various phosphorus-containing substances were employed instead of silica-alumina. The data are presented in the following Table 6. From an examination of the data, it is apparent that these phosphorus-containing substances are effective catalysts in the production of DMDEE from HEM.

TABLE 6

| Ex. No. | HEM moles | Catalyst Type | wt.% | Temp.[4] °C. | Time, hrs. | % HEM conv. | Lts. (H$_2$O, etc.) | HEM | By-products[3] | DMORE | DMDEE | Hvys. | DMDEE/DMORE |
|---|---|---|---|---|---|---|---|---|---|---|---|---|---|
| 29 | 3.50 | T-1563[1] | 1.0 | 259 | 5.0 | 55.3 | 0.8 | 44.6 | 2.0 | 8.9 | 42.2 | 1.4 | 4.8 |
| 30 | 3.50 | T-1510 | 1.0 | 239 | 5.0 | 43.9 | 1.3 | 56.1 | 0.8 | 10.5 | 30.7 | 0.3 | 2.9 |
| 31 | 1.85 | H$_3$PO$_3$[2] | 1.0 | 241 | 5.0 | 32.0 | 1.3 | 68.0 | 0.3 | 3.1 | 26.7 | 0.6 | 8.7 |
| 32 | 1.85 | H$_3$PO$_3$ | 2.5 | 241 | 5.0 | 49.0 | 2.8 | 51.0 | 0.7 | 5.4 | 38.9 | 1.2 | 7.1 |
| 33 | 1.85 | H$_3$PO$_3$ | 5.0 | 240 | 5.0 | 68.8 | 6.3 | 31.2 | 1.1 | 12.7 | 47.9 | 0.6 | 3.8 |
| 34 | 3.50 | BPO$_4$ | 5.0 | 241 | 5.0 | 60.4 | 1.2 | 39.6 | 0.1 | 25.6 | 31.5 | 1.0 | 1.2 |
| 35 | 3.50 | FePO$_4$ | 5.0 | 258 | 5.0 | 65.0 | 0.8 | 35.0 | 2.4 | 12.7 | 46.5 | 2.4 | 3.7 |

[1]20% phosphoric acid on silica, Girdler
[2]Charged as aqueous 30% phosphorous acid
[3]Predominantly aminoethoxyethylmorpholine and hydroxyethyoxyethylmorpholine.
[4]Back pressure regulator set at ca 50 psig
[5]Vented material disregarded; ranged from 0.0-4.8% of liquid charge and consisted of approximately 20-85% water.

EXAMPLE 36

In the following example a C-(substituted) bis-(morpholino-N-alkyl) ether was produced in accordance with the invention. According to the general procedure of Examples 1-7, N-(2-hydroxyethyl)-2,6-dimethylmorpholine was charged into a 1-liter stirred autoclave along with 15.0 wt. % Aerocat ® TA and held for six hours at 260° C. A GLC A% analysis of the product mixture showed a 66.85% conversion of starting material of which 88.2% was tetramethyl-DMDEE and 10.8% was tetramethyl-DMORE. Distillation of the reaction mixture through an 8" vacuum jacketed silvered Vigreux column gave a 99.29% pure sample of tetramethyl-DMDEE which was identified by its physical and spectral properties.

EXAMPLE 37-38

The following examples were run for comparison to show how unexpectedly selective the inventive process While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for producing a bis-(morpholino-N-alkyl) ether compound from the corresponding N-(hydroxyalkyl)morpholine compound, said N-(hydroxyalkyl)morpholine compound having the formula:

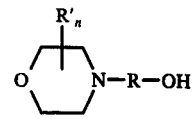

wherein R is a straight chain or a branched chain alkyl radical of from 2 to 10 carbon atoms, R' is a lower alkyl radical, and n is an integer from 0 to 4 comprising the steps of:

contacting said N-(hydroxyalkyl)morpholine compound with a catalytically effective amount of a phosphorus-containing substance selected from the group consisting of acidic metal phosphates, phosphoric acids and their anhydrides, or phosphorous acids and their anhydrides, alkyl or aryl phosphate esters, alkyl or aryl phosphite esters, alkyl or aryl substituted phosphorous and phosphoric acids, alkali metal monosalts of phosphoric acid, the thioanalogs of the foregoing, phosphoric acid-impregnated silicas having from about 10 to about 30 wt. % phosphoric acid and mixtures thereof, at a temperature of from about 200° C to about 300° C under a pressure sufficient to maintain the mixture substantially in liquid phase; and recovering said bis-(morpholino-N-alkyl) ether compound from the reaction mixture.

2. The process according to claim 1 wherein said catalyst is a phosphoric acid-impregnated silica having from about 5 to about 30 wt. % phosphoric acid.

3. The process according to claim 1 wherein said phosphorus-containing substance is phosphorous acid in an aqueous solution in an amount of from about 5 to about 70 wt. %.

4. The process according to claim 1 wherein said phosphorus-containing substance is ferric phosphate.

5. The process according to claim 1 wherein said phosphorus-containing substance is boron phosphate.

6. The process according to claim 1 wherein said phosphorus-containing substance is aluminum phosphate.

7. The process according to claim 1 wherein said contacting is carried out at a temperature of from about 240° C to about 280° C.

8. The process according to claim 1 wherein R and R', are independently, alkyl radicals having from 2 to 3 carbon atoms.

9. The process according to claim 1 wherein said contacting is effected at a pressure of from about 10 to about 1000 psig and wherein water is continuously removed from the reaction zone as a vapor as it is formed in the condensation reaction.

10. The process according to claim 1 wherein said contacting is carried out at a temperature of from about 255° C to about 265° C.

11. The process according to claim 1 wherein said N-(hydroxyalkyl)morpholine is N-(2-hydroxyethyl)-2,6-dimethylmorpholine and N,N'-bis(2,6-dimethylmorpholinoethyl)ether is recovered from the reaction mixture.

12. The process according to claim 1 wherein said N-(hydroxyalkyl)morpholine is N-(2-hydroxyethyl)morpholine, and N,N'-(dimorpholinodiethyl)ether is recovered from the reaction mixture.

13. The process according to claim 1 wherein said N-(hydroxyalkyl)morpholine is N-(2-hydroxypropyl)morpholine and N,N'-(dimorpholinodiisopropyl)ether is recovered from the reaction mixture.

* * * * *